(12) United States Patent
Gill et al.

(10) Patent No.: US 9,753,024 B2
(45) Date of Patent: Sep. 5, 2017

(54) BLOOD COAGULOMETER AND METHOD

(71) Applicant: Board of Regents The University of Texas System, Austin, TX (US)

(72) Inventors: Brijesh S. Gill, Houston, TX (US); Kevin Aroom, Houston, TX (US); Charles Cox, Jr., Bellaire, TX (US)

(73) Assignee: Board of Regents of the University of Texas Systems, Austin, TX (US)

( * ) Notice: Subject to any disclaimer, the term of this patent is extended or adjusted under 35 U.S.C. 154(b) by 272 days.

(21) Appl. No.: 14/427,235

(22) PCT Filed: Sep. 11, 2013

(86) PCT No.: PCT/US2013/059286
§ 371 (c)(1),
(2) Date: Mar. 10, 2015

(87) PCT Pub. No.: WO2014/043251
PCT Pub. Date: Mar. 20, 2014

(65) Prior Publication Data
US 2015/0226725 A1 Aug. 13, 2015

Related U.S. Application Data

(60) Provisional application No. 61/699,494, filed on Sep. 11, 2012.

(51) Int. Cl.
*G01N 33/49* (2006.01)
*G01N 11/10* (2006.01)
*G01N 11/16* (2006.01)

(52) U.S. Cl.
CPC ............. *G01N 33/49* (2013.01); *G01N 11/10* (2013.01); *G01N 33/4905* (2013.01); *G01N 11/16* (2013.01)

(58) Field of Classification Search
CPC .... G01N 33/49; G01N 11/10; G01N 33/4905; G01N 11/16
See application file for complete search history.

(56) References Cited

U.S. PATENT DOCUMENTS 3,967,934 A * 7/1976 Seitz ...................... G01N 11/10
422/73
4,328,701 A 5/1982 Mau-Tung et al.
(Continued)

FOREIGN PATENT DOCUMENTS

GB 1353481 A 5/1974
WO 2014043251 A1 3/2014

OTHER PUBLICATIONS

International Searching Authority (ISA); International Search Report and Written Opinion; Dec. 18, 2013.
(Continued)

*Primary Examiner* — Hezron E Williams
*Assistant Examiner* — David Z Huang
(74) *Attorney, Agent, or Firm* — Patrick K. Steele

(57) ABSTRACT

An apparatus for determining blood clotting capacity comprises an actuator to cyclically move a member within a sample of blood received in a well in a tray and one of a deflection sensor and a position sensor to determine the position of the wetted member upon being acted upon by the actuator. The theoretical position of the wetted member, as determined using a known actuator force and wetted member physical data, is compared to the sensed deflection or position of the wetted member, and the resistance to movement of the wetted member caused by the blood is determined and correlated to a clotting capacity.

21 Claims, 8 Drawing Sheets

(56) References Cited

U.S. PATENT DOCUMENTS

| | | | | |
|---|---|---|---|---|
| 5,293,772 | A | * | 3/1994 | Carr, Jr. ............. G01N 33/4905 422/73 |
| 6,711,943 | B1 | * | 3/2004 | Schob ................... A61M 1/101 73/54.28 |
| 2006/0034734 | A1 | * | 2/2006 | Schubert ............ G01N 33/4905 422/430 |

OTHER PUBLICATIONS

Database WPI; Week 201341; Thompson Scientific, London, GB; Jul. 3, 2012.

* cited by examiner

BLOOD COAGULOMETER AND METHOD

STATEMENT OF RELATED APPLICATIONS

This application depends from and claims priority to U.S. Provisional Patent Application Ser. No. 61/699,494 entitled Blood Coagulometer filed on 11 Sep. 2012.

FIELD OF THE INVENTION

This application relates to an apparatus and a method for determining the clotting capacity of a sample of blood.

BACKGROUND OF THE INVENTION

The process of blood coagulation (thrombogenesis) results in blood dotting and involves a coagulation cascade of many factors most of which are enzymes which cleave downstream proteins in the coagulation process. The ability to maintain proper clotting balance is critical. Disorders that effect coagulation of blood can lead to uncontrolled bleeding (hemorrhage) or uncontrolled clotting (thrombosis) that can prevent blood flow to critical organs such as, for example, the heart or the brain.

Many tests are available to evaluate the function of the clotting system in mammals. Currently, one of the most informative methods of testing the efficiency of the dotting system is thromboelastography ("TEG"). For a recent review see Trapani, L., "Thromboelastography: Current Applications, Future Directions," *Open Journal of Anesthesiology*, January 2013. TEG, in its original format, uses a sample of blood that is placed in a cuvette and rotated about a thin wire (wetted member) that measures clot formation, clot strength and other parameters. In an alternate form, known as rotational thromboelastometry (ROTEM), the sample remains stationary, but the shaft includes a sensor pin to measure various parameters as the shaft rotates within the well in which the blood sample is disposed. Conventional TEG devices are large and expensive, which limits their availability. The basic mechanism and design of conventional TEG devices is not conducive to miniaturization.

The presently described methods and devices provide a novel mechanism and device to measure blood coagulation parameters which represents a microelectromechanical system (MEMS). The miniaturization possible with this design allows the device to be constructed as a single-use sealed and disposable with or without all electronics built into the package. This offers many advantages, including but not limited to, a reduction in the volume of the blood sample required, the expense of the test and allows bedside (point of care) application and enhances both safety and convenience.

SUMMARY OF THE PRESENT INVENTION

The present invention relates to an apparatus to measure clotting in a blood sample, comprising a tray, a well in the tray to receive a sample of the blood, a support beam connected at a first end to the tray and connected at a second end to a wetted member to support the wetted member at least partially within the well, a linear motor connected between the tray and the support beam and activatable by application of an electrical current to impart a force, corresponding in magnitude to the applied current, on the support beam to move the support beam relative to the tray and to thereby move the wetted member within the well, and a deflection sensor coupled to the tray to measure the deflection of the support beam resulting from resistance to movement of the wetted member imparted by the sample of blood received in the well, wherein the measured deflection of the support beam resulting from the resistance to movement of the wetted member within the sample of blood in the well is correlated to a capacity of the blood to clot. An embodiment of the apparatus may include an electrically-powered linear motor having at least one conductive coil through which the electrical current flows, and at least one magnet disposed on a connecting rod movable within the at least one conductive coil, wherein the application of an electrical current having a first polarity to the linear motor causes the connecting rod to be moved in a first direction against the support beam, and wherein the application of an electrical current having a second polarity, opposite to the first current, causes the connecting rod to be moved in a direction opposite to the first direction. An embodiment of the apparatus may include a support beam that is an elastically flexible elongate shaft. An embodiment of the apparatus may include an electrically-powered linear motor that is connectable to a battery, and the tray may comprise a battery portion to receive and secure a battery to the tray. An embodiment of the apparatus may include a deflection sensor comprising a laser element coupled to the tray to generate an incident beam, a reflective member on the support beam, and a photo-detector array coupled to the tray and connectable to a controller wherein the photo-detector array generates a signal to the controller indicating the location of impingement on the photo-detector array of a reflected beam, and the signal enables the determination of the angle between the incident beam and the reflected beam, wherein the angle between the incident beam and the reflected beam indicates the deflection of the support beam as a result of the resistance to movement of the wetted member connected to the support beam within the well as a result of the force imparted by the linear motor to the support beam, and wherein the angle can be correlated to the clotting capacity of the blood. An embodiment of the apparatus may include a deflection sensor that comprises a strain gauge coupled to the support beam to generate a signal to a processor corresponding to the stress imparted to the support beam as a result of the resistance to movement of the wetted member within the well as a result of the force imparted by the linear motor to the support beam, wherein the signal generated by the strain gauge can be correlated to the clotting capacity of the blood. An embodiment of the apparatus may include a controller to receive a signal corresponding to the measured deflection and generated by the deflection sensor and to generate a display signal, and a display device coupled to the tray and connected to receive the display signal from the controller. The display device may be, for example, a light emitting diode display device, a liquid crystal display device or a gauge.

An alternative embodiment of the device to measure the capacity of a sample of blood to clot may comprise a tray, a well in the tray to receive a sample of the blood, a carriage, having a first end, a second end, a magnetic material and a wetted member movably supported on the tray to support at least a portion of the wetted member within the well of the tray, and a motor comprising at least a first electromagnet connectable to an electrical current source, wherein electrically energizing the first electromagnet creates a magnetic field that imparts a corresponding force on the magnetic material of the carriage to move the carriage and to move the wetted member within the well. An embodiment of the apparatus may include a motor that further comprises a second electromagnet connectable to an electrical current source, wherein electrically energizing the first and second electromagnets creates a magnetic field that imparts a corresponding force on the magnetic material of the carriage to move the carriage and to move the wetted member within the well. An embodiment of the deflection sensor of the apparatus may comprise an image sensor disposed on an interior side of a tray cover to detect the position of the carriage and to generate a signal to a controller indicating the position of the carriage, wherein the controller receives the signal indicating the location of the position of the carriage resulting from the force applied to the magnetic material of the carriage, and wherein the controller compares the calculated position of the carriage to a theoretical position of the carriage determined based on the carriage mass and the known force applied to the magnetic material by the first electromagnet. An embodiment of the apparatus may include the controller comparing the theoretical position of the carriage and the detected position of the carriage to indicate the clotting capacity of the sample of blood received in the well. An embodiment of the apparatus may include a controller to receive a signal corresponding to the sensed position of the carriage and generated by the image sensor and to generate a display signal, and a display device that may be coupled to the tray and connected to receive the display signal from the controller. An embodiment of the apparatus may include a display device that is one of a light emitting diode display device, a liquid crystal display device and a gauge.

It will be understood that the components of the deflection sensor 27 described above could be adapted for use in determining the position of the carriage even though there is no actual "deflection" to be measured. For example, a laser light source or laser element, a reflective member on the carriage, and a photo-detector array could be used to determine the position of the carriage that supports the wetted member within the well and that is moved by activation of adjacent electromagnets if the reflective member on the carriage has a known, constant and non-perpendicular orientation relative to the laser element. The non-perpendicular orientation of the reflective member causes the actual portion of the reflective member that reflects the incident beam to vary in its distance from the laser element. This variance will cause the reflected beam to impinge on the photo-detector array at varying locations indicating the position of the carriage.

An embodiment of a method of testing a sample of blood to determine the dotting capacity of the blood comprises the steps of providing a base having a well, receiving, into the well, a sample of the blood to be analyzed, connecting a wetted member to a first portion of a support member, movably supporting the support member on the base and above an interface between the sample of blood and air to dispose at least a portion of the wetted member within the sample of blood and below the interface, imparting a known force to the support member to displace the portion of the support member and the wetted member connected thereto relative to the well to move the wetted member within the sample of blood, determining a theoretical displacement of the wetted member corresponding to the known force imparted to the support member, measuring the displacement of the wetted member as a result of the known force imparted to the support member, comparing the measured displacement of the wetted member within the sample of blood to the theoretical displacement to determine a resistance to displacement of the wetted member attributable to the sample of blood, and correlating the resistance to displacement of the wetted member to a dotting capacity of the sample of blood. The method may further include the steps of imparting a second known force to the support member, determining a theoretical displacement of the wetted member corresponding to the second known force imparted to the support member, measuring the displacement of the wetted member as a result of the second known force imparted to the support member, comparing the measured displacement of the wetted member within the sample of blood to the theoretical displacement to determine a resistance to displacement of the wetted member attributable to the sample of blood, and correlating the resistance to displacement of the wetted member to a clotting capacity of the sample of blood. The second known force may be equal to the previously imparted known force.

DETAILED DESCRIPTION OF PREFERRED EMBODIMENTS

Figure 1:
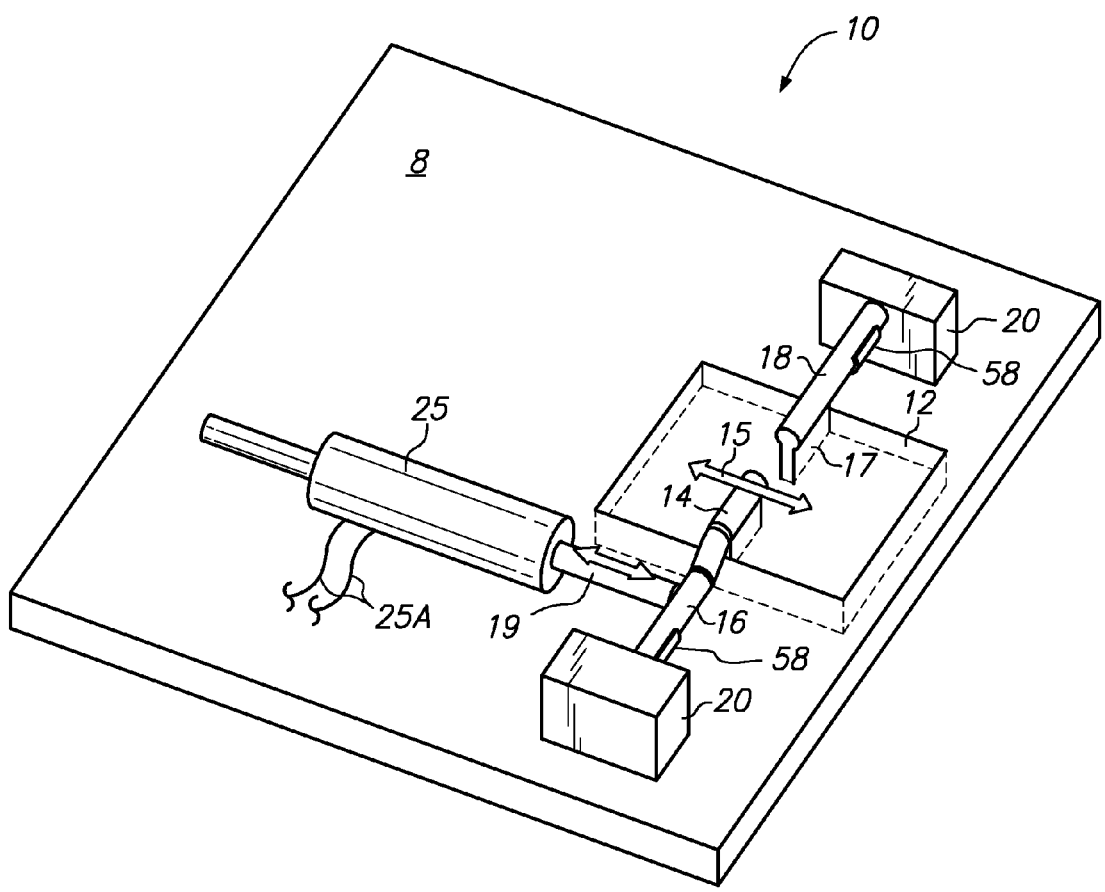
FIG. 1 is a perspective view of an embodiment of a blood coagulometer of the present invention.

The present invention provides an apparatus to determine the clotting capacity of a sample of blood and a method of determining the capacity of a sample of blood to coagulate, or clot. The operation of the apparatus of the present invention, and the operation of the related method, require an understanding of the blood changes that occur within a blood sample as blood coagulates and clots.

Blood clots by formation of a network of polymerized fibrins. A circulating monomer called fibrinogen is induced to polymerize into fibrin, which forms the physical clot. Fibrins bind one to the others and form a network of fibrins, or a fibrin skeleton. Increasing fibrin polymerization results in a change in the viscosity of the clotting blood and, with increasing fibrin network binding, the clot begins to behave as a solid composite as opposed to behaving as a fluid.

A structural member can be introduced into the blood and moved through the blood. This structural member, or wetted member, displaced through a clotting sample of blood pushes the fluid component of blood aside as it moves through the blood. The resistance attributable to the fluid component of the blood is well known in rheology. In addition, however, there is an added component of resistance to movement of a wetted member through the blood caused by the network of increasingly interconnected fibrins. The increasingly interconnected fibrins do not behave as a fluid, and the component of the total resistance to movement of a wetted member through a sample of clotting blood attributable to the increasingly interconnected fibrins will soon be the dominant component of resistance to movement of the wetted member.

It will be understood that the component of resistance to movement of a wetted member through a sample of clotting blood attributable to the fluid component of the blood is a primarily a function of the viscosity and density of the blood (for a wetted member of constant size and configuration). The component of resistance to movement of a wetted member through a sample of clotting blood attributable to the formation of a network of fibrins, however, is also determinable. Because the network of fibrins behaves more like a solid than like a fluid, the resistance to movement of a wetted member can be analyzed as if the wetted member compresses a compressible solid as it moves through the sample of blood.

Just as the size and configuration of the wetted member is to be considered in determining the component of the resistance to movement of the wetted member through a fluid, the size and configuration of the wetted member is also important in analyzing the component or resistance to movement of the wetted member as it compresses the network of fibrins in the sample of blood. For example, assuming L is 5 microns (L refers to the dimension of the material being compressed in the direction of compression, which is limited by the width of the well and is the distance from the wall to the portion of the primary wetted member that moves into and against the clot for a sample of blood), and assuming a clot modulus of 1,000 dynes per square centimeter, then the force required for 20% compression (i.e., 20% of 5 microns, or 1 microns) can be determined by:

$$\delta = \frac{\text{Force} * \text{Length}}{\text{Modulus} * \text{Area}} = 10^{-6} \text{ m}$$
$$\text{Modulus} = E = 1000 \text{ dynes/cm}^2 = 100 \text{ Pa} = 100 \text{ N/m}^2$$
$$F = \frac{\delta * E * A}{L} = \frac{10^{-6} * 100 * (5*10^{-6})^2}{5*10^{-6}} = 5*10^{-10} \text{N} = 0.0005 \text{ }\mu\text{N}$$

Although blood is a non-Newtonian fluid, observations can be made that simplify this calculation. Blood exhibits its non-linear behavior via shear thinning, and maximum viscosity is seen at low-flow velocities, as seen in capillaries. It should be noted that the low-flow velocities seen in capillaries is the flow regime that conventional thromboelastography ("TEG") devices attempt to emulate. In this flow regime, blood flow is considered to be purely laminar, with a Re~0.01 or less as determined by experimental results. The velocity of blood flow in human capillaries is variable, but a generally accepted number is roughly 1 mm/sec.

If we presume that the face of the wetted member that is incident to the blood is not purely planar, but instead has a forward projection directed into the direction of flow through the sample of blood, then the Navier-Stokes equations simplify to Stokes' law (for the calculation to be exact, the forward face of the wetted member should be a hemisphere, but a cylinder or a pyramid would be of similar order of magnitude): $F=-6*\pi*\eta*r*v$ If we assume dynamic viscosity=0.02 Pa sec (20 centipoise, experimentally determined in congestive heart failure patients; this is the highest viscosity generally found in related literature, with a normal viscosity being an order of magnitude less), and if we assume an effective radius of 20 microns and a velocity of 2.5 mm/sec, the equation becomes:

$$F=-6\pi*0.02*20\times10^{-6}*2.5\times10^{-3}=2\times10^{-8} \text{ N}=0.02 \text{ }\mu\text{N}$$

The design of the well is motivated by the following consideration: if the force required for clot compression is very small compared to the hydrodynamic forces, then there will be very little change in resistance to wetted member movement when a clot forms, i.e., when the network of fibrins is created within the blood sample. Revisiting the compression equation for a displacement 50 microns (an actuator stroke typically achievable in microelectromechanical systems ("MEMS")) and for a cross-sectional area of the proposed wetted member of 10,000 square microns (for example, 100 microns×100 microns), and ignoring for now that the wetted member will only be partially submerged), the equation becomes:

$$\delta = \frac{\text{Force}*\text{Length}}{\text{Modulus}*\text{Area}} = 10^{-6} \text{ m}$$
$$\text{Modulus} = E = 1000 \text{ dynes/cm}^2 = 100 \text{ Pa} = 100 \text{ N/m}^2$$
$$F = \frac{\delta*E*A}{L} = \frac{50*10^{-6}*100*(1*10^{-4})^2}{L} = \frac{5*10^{-11}}{L}\text{N}$$

Thus, for example, the force required to compress a clot through a 50 micron displacement of the actuator would decrease as the well width increases (and, thus L, because a 50 micron displacement would represent a decreasing percentage of the starting total width of the clot). With one possible embodiment of the wetted member configuration, the Stokes' drag force and the compression force become similar as the well width approaches 1 mm, which is represented by the width of the central portion of the well in the blood coagulometer illustrated in FIGS. 4 and 5 appended hereto.

It should be noted that the compression force requirement increases with the area of the face of the wetted member, while the Stokes' drag increases with the diameter. As a result, using a larger wetted member (up to 100 microns in size) makes these approximations more accurate, however, at some point the size of the wetted member will become difficult to manufacture via standard MEMS methods. Similarly, as the wetted member gets smaller, the drag forces will overwhelm the clot compression forces because the compression forces get smaller much faster than the drag forces.

This analytical approach can be used in connection with a blood coagulometer as described in more detail below and as depicted in the drawings appended hereto. It will be understood that the drawings depict only a few embodiments of the blood coagulometer of the present invention, and that the actual scope of the present invention is limited only by the claims.

Embodiments of the blood coagulometer and method of the present invention measure the coagulation of a sample of blood, and comprise a wetted member, having a known size and configuration, that is driven to move and/or reciprocate within a sample of coagulating blood disposed in a well. As the enzymatic coagulation cascade produces a cross-linked fibrin network that forms a clot in the blood sample, the wetted member encounters increasing resistance to movement through the clotting blood sample. The increasing resistance to movement of the wetted member due to clotting within the sample of blood reduces the movement of the wetted member for a known drive current provided to the actuator to produce a known force applied to the structure that supports the wetted member. The theoretical displacement of the wetted member is determined based on the physical characteristics of the support member (i.e. size and configuration), and the actual displacement of the wetted member is determined by use of a sensor. The measurable decrease in movement attributable to clotting, determined as the difference between the theoretical displacement and the measured displacement of the wetted member, enables the quantification of the blood coagulation process over time; that is, the movement of the wetted member (or lack thereof) when acted upon by a force of known direction and magnitude reveals the kinetics of the overall coagulation reaction in the sample of blood.

As clot lysis occurs, an increase in the movement of the wetted member (i.e., a decrease in the resistance to movement of the wetted member) in response to a known force applied to the support member is restored until the sample of blood is back at baseline resistance attributable to the fluid, reflecting the completion of the coagulation/fibrinolysis cycle.

In one embodiment of the blood coagulometer of the present invention, the wetted member is suspended from a portion, such as an end, of a support beam. The wetted member is connected to the support beam so that at least a portion of the wetted member descends from the support beam into the well and at least partially into a sample of blood received in the well. A current-activated linear actuator is connected between the tray or base and the support beam. For example, the linear actuator may be connected between the tray or base at a first end and a connector fixed on the support beam at a second end. Upon activation, the linear actuator displaces the connector and the support beam in response to a known current delivered to the actuator. The displacement of the wetted member within the sample of blood is measured by, for example, measuring the deflection of the support beam that results from the application of the actuator force at a first portion of the support beam, proximal to the first end of the support beam, and the resistance to movement of the wetted member, at the second end of the support beam, within the sample of blood.

In another embodiment of the blood coagulometer of the present invention, the wetted member is suspended from a portion of a carriage that supports the wetted member. The carriage may comprise a retainer to support the wetted member, a first low friction support member to support a first end of the retainer, a second low friction support member to support a second end of the retainer, and a magnetic material to cooperate with a magnetic field to move the carriage using a known force. The wetted member is connected to the portion of the carriage so that at least a portion of the wetted member descends from the carriage into the well and at least partially into the sample of blood. An electromagnet is connected to the tray or base and activated, using a known current, to impart a known force to the carriage to displace the carriage and to move the wetted member supported therefrom in response to the known current delivered to the electromagnet. The displacement of the wetted member within the sample of blood is measured by, for example, measuring the actual displacement of the carriage as a result of exposure to the known magnetic force applied by the electromagnet as reduced by the resistance to movement of the wetted member within the sample of blood.

FIGS. 1-8 illustrate embodiments, or portions of embodiments, of the apparatus and method of the present invention.

FIG. 1 is a perspective view of some of the components of an embodiment of a blood coagulometer 10 of the present invention. The deflection sensor is omitted from FIG. 1 so that the remaining components (tray, actuator, support beam, primary wetted member and secondary wetted member) can be seen clearly, and the deflection sensor is added in FIG. 2 to complete the illustration. The embodiment of the apparatus of FIG. 1 includes a tray 8, and a well 12 to receive a sample of blood. The blood sample is not shown in FIG. 1 to better reveal the components of the embodiment of the blood coagulometer 10. The embodiment of the blood coagulometer 10 of FIG. 1 further comprises a primary wetted member 14 supported within the well 12 by a support beam 16. The support beam 16 may be statically or pivotally coupled to stationary member 20 and movable by an actuator 25 to move the primary wetted member 14 back and forth within the well 12 and along a path generally indicated by the double-headed arrow 15. It will be understood that the primary wetted member 14 is at least partially immersed in a sample of blood when the sample of blood is received into the well 12.

The secondary wetted member 17 is supported within the well 12 by a secondary support beam 18 and is substantially similar in structure to the primary wetted member 14, but is simply positioned within the well 12 to be acted upon by the blood sample (not shown) in the well 12 and not driven to move by an actuator 25, as is the primary wetted member 14. Rather, the secondary wetted member 17 moves under the influence of the clotting blood sample (not shown) in the well 12 and by the movement of the dotting blood sample by the actuator 25 and the actuator-driven primary wetted member 14. Secondary support beam 18 statically or pivotally coupled to stationary member 20. The secondary wetted member 17 allows the measurement of clot adhesion, as is necessary to occur for a clot to provide hemostasis in attaching itself to a wall of a lacerated blood vessel. In one embodiment, the surface of the secondary wetted member 17 is conditioned or treated with, for example, tissue factor (also known as platelet tissue factor, factor III or thromboplastin) or collagen to aid the measurement of clot adhesion (as such are not normally present in the absence of vessel wall disruption) by observing movement of the secondary wetted member 17 induced by movement of the adhered blood clot under the influence of the movement of the adjacent primary wetted member 14.

Figure 2:
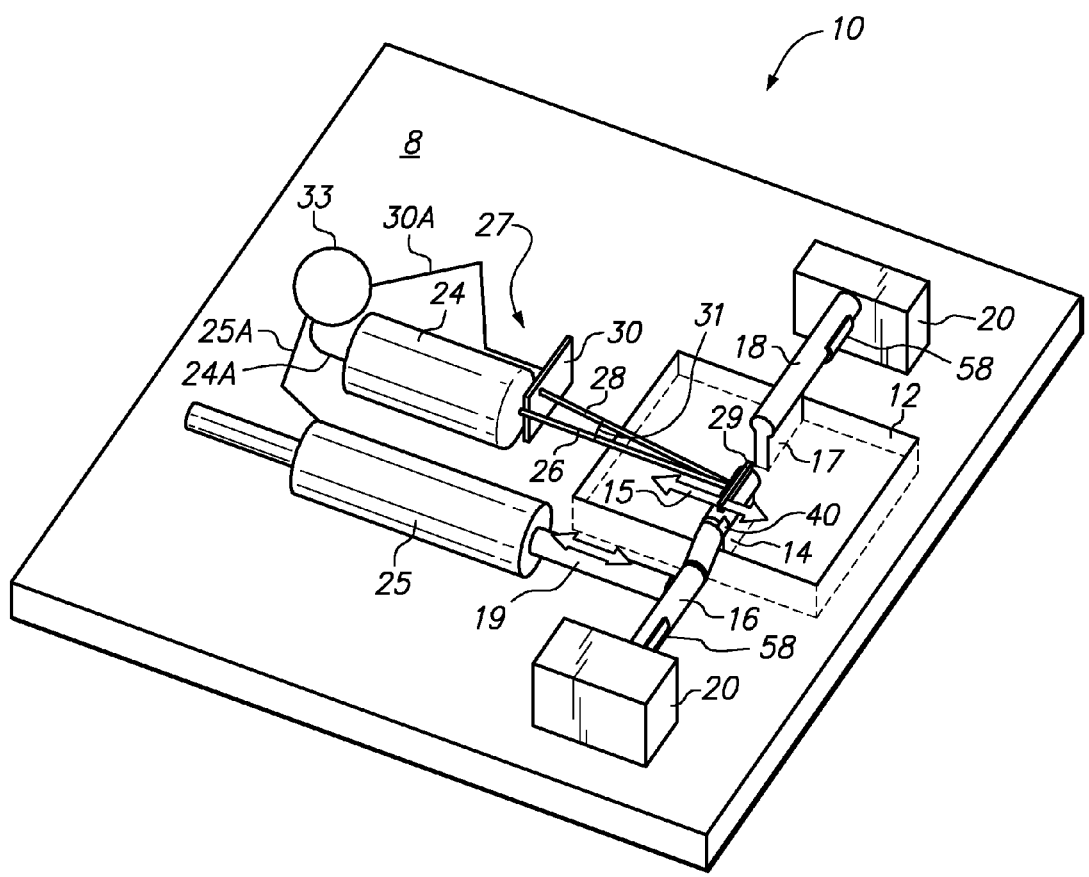
FIG. 2 is a perspective view of an embodiment of a blood coagulometer of the present invention with a position sensor.

The support beam 16 supports the primary wetted member 14 within the well 12 and couples the actuator 25 to the primary wetted member 14, allowing the primary wetted member 14 to be driven through the blood sample (not shown) received within the well 12. The primary characteristics of the support beam 16 are stiffness and elasticity, so that the support beam 16 deflects easily when acted upon by the actuator 25 but without the requirement of undue current provided to the actuator 25 via wires 25A. The bending of the support beam 16, when driven by the actuator 25, allows movement of the primary wetted member 14 to be read quantitatively by the deflection sensor 27, which is illustrated in FIG. 2.

The secondary wetted member 17 is supported within the well 12 by a secondary support beam 18. In a preferred embodiment, the secondary support beam 18 has less stiffness than the primary support beam 16. Both the primary support beam 16 and the secondary support beam 18 are statically or pivotally connected at one end by a stationary member 20, which is coupled to the tray 8 and fixed relative to the well 12 in the tray 8.

The actuator 25 is coupled to the connecting rod 19 and used to drive the movement of the primary support beam 16. The actuator 25 can be any linear actuator or perhaps a rotational actuator with a linkage for converting rotary movement to reciprocal movement. A preferred embodiment includes an electromagnetic actuator because it provides for a smooth and continuous variation of the position of the primary wetted member 14 through the primary support beam 14 and, using processor-controlled electrical current input through wires 25A, can impart any desired waveform to the resulting movement of the primary wetted member 14.

It should be noted that for conventional thromboelastography ("TEG") devices, the well 12 is generally cylindrically-shaped because of the rotational movement of the torsion-wire apparatus. However, embodiments of the micro-electromechanical blood coagulometer of the present invention allow the well 12 to be of a variety of cross-sectional shapes. The shape of a toroidal section may be preferred to minimize the required volume of the blood sample and to allow natural motion of the primary measurement wetted member 14 as it swings through the sample on the end of the support beam 16.

The well 12 of embodiments of the blood coagulometer 10 of the present invention is relatively shallow to minimize the required volume of the blood sample. A shallow well 12 also aids in the production of the blood coagulometer 10 using a micro-scale manufacturing processes. Some minimum blood sample volume is necessary because of the composite nature of a blood clot which contains red blood cells (diameter approximately 8 microns) trapped in a three-dimensional matrix of cross-linked fibrin and platelet aggregates. The well 12 may be preloaded with a clot activator such as, for example, kaolin, as used in the rapid TEG assay, to reduce the length of the time required to complete the coagulation process.

The primary wetted member 14 and secondary wetted member 17 in FIG. 1 provide interaction of the actuator 25 with the blood sample (not shown). The movement of the primary wetted member 14 agitates the blood sample (not shown) mimicking the situation found in vivo where increasing shear is known to activate coagulation. Resistance to movement of the primary wetted member 14 as a blood clot forms allows the determination of the coagulation profile.

The primary wetted member 14 is, in its simplest incarnation, a rounded cylinder which glides through the blood sample (not shown) prior to coagulation. Alternative shapes for the primary wetted member 14 include, but are not limited to, a rectangular cross section or a pyramidal cross section. The cross sectional dimensions of the primary wetted member 14 are chosen to be larger than the erythrocyte (RBC) diameter of 8 microns and, preferably, substantially larger, in order to impart to the primary wetted member 14 the ultra-structural characteristics of the blood clot overall, rather than some local phenomenon in an anisotropic medium.

The primary wetted member 14 can be functionalized by binding antibodies to its surface to impart to the primary wetted member 14 specific biological clotting characteristics. For example, antibodies to known platelet membrane glycoproteins could be used to bind platelets to the surface of the primary wetted member 14 and, depending on the platelet receptors chosen, induce or alter coagulation within the blood sample. The primary wetted member 14 can be made of many different materials, and is preferably rigid compared to the clot, although in practice this is easily achieved with a wide variety of materials due to the compliant nature of dotted blood. The use of an electromagnetic actuator 25 allows large forces to be generated to allow a wider range of measurement regimes, including disruptive destructive measurements that may reflect the situation in vivo during life-threatening hemorrhage, but which are not measured using current blood coagulometer technology.

The connecting rod 19 connecting the actuator 25 to the primary support beam 16 may be a rigid shaft that serves to couple the action of the actuator 25 to the primary support beam 16. An alternative embodiment may include one or more electromagnets disposed on either side of the primary support beam 16 and one or more magnetic materials on or within the primary support beam 16. Such an arrangement would eliminate the need for the connecting rod 19. Such a design is more complex because of the larger number and arrangement of magnets required, but may be preferred since the "push-pull" configuration using electromagnets frees the support beam 16 from being required to function as a return spring. The incorporation of electromagnets into alternate embodiments of the blood coagulometer 10 of the present invention is discussed in more detail below. Strain gauges 58 may be provided on one or both of primary support beam 16 and secondary support beam 18 to generate a signal provided through wires (not shown) to a processor (not shown) indicating the deflection of the support beam 16 and/or the secondary support beam 18, as will be discussed in more detail below. It should be understood that a strain gauge 58 may be used in place of or in addition to other deflection sensors.

There are several possible techniques to measure deflection of the primary support beam 16, two of which are illustrated in the drawings appended hereto. FIG. 2 is a perspective view of the embodiment of a blood coagulometer 10 of FIG. 1 with an alternate deflection sensor 27 to sense the deflection of the primary support beam 16 that supports the primary wetted member 14 in the well 12 of the tray 8. The deflection sensor 27 illustrated in FIG. 2 uses the reflection of an incident beam 26 of laser light emitted from a laser element 24 and reflected off of a reflective member 29 on the primary support beam 16. As the primary support beam 16 or the primary wetted member 14 deflects due to resistance to movement of the primary wetted member 14 within the sample of blood, the incident beam 26 reflects through an angle 31 that changes (grows) with the magnitude of deflection of the support beam 16. The reflected beam 28 impinges on a photo-detector array 30 that measures the angle 31 and, hence, indicates the deflection of the primary support beam 16 or the primary wetted member 14 that is required to produce the measured angle 31.

Alternately, or in addition to the laser element 24 and photo-detector array 27 measurement components, the deflection of the primary support beam 16 or the primary wetted member 14 may be measured by attaching a strain gauge 58 to the primary support beam 16 and/or to the secondary support beam 18. This technique allows a direct electrical resistance measurement that indicates the deflection of the primary support beam 16, and which deflection can be correlated to the resistance to movement of the primary wetted member 14. Similarly, a strain gauge 58 on the secondary support beam 18 allows a direct electrical resistance measurement that indicates the deflection of the secondary support beam 18 caused by movement of the secondary wetted member 17 by transfer of at least some of the movement of the primary wetted member 14 through the dotting blood (not shown). This technique potentially simplifies the overall system design, but may increase the complexity of the secondary support beam 16, the secondary support beam 18 or the primary wetted member 14. It should be noted that strain gauges may be disposed at alternate or multiple locations on the primary support beam 16 and/or secondary support beam 18, as is illustrated by second strain gauge 40 on the primary support beam 16.

Another alternative measurement technique involves the fabrication of the blood coagulometer 10 as shown on a transparent tray 8 or substrate so that a light source on the bottom of or underneath the tray 8 of the apparatus 10 can impinge light on a photo-detector array (not shown) on top side of the apparatus 10. This technique allows simpler direct measurement of the deflection of the primary support beam 16, but may be costlier to manufacture.

For these embodiments that include a deflection measurement technique, components of the deflection sensor 27 such as, for example, the laser element 24, the photo-detector array 30 and the actuator 25, may be connected to a controller 33 via suitable signal conditioning electronics, which are not shown in FIG. 2. That is, the controller 33 generates a signal 25A that activates the actuator 25 to move the primary support beam 16 at a desired displacement, waveform, frequency or rate, thereby resulting in deflection of the primary support beam 16 and movement of the primary wetted member 14 within the blood sample (not shown) in the well 12. The controller 33 may also activate the laser element 24 to produce an incident beam 26 that impinges on the reflective member 29 on the primary support beam 16. The deflection of the primary support beam 16 causes an angle 31 between the incident beam 26 and the reflected beam 28. The photo-detector array 30 generates a signal 30A to the controller 33 that corresponds to the location on the photo-detector array 30 of the reflected beam 28. It will be understood that the controller 33 may determine the angle 31 based on the location of the reflected beam 28 on the photo-detector array 30 and the controller 33 may generate a signal to a display device (not shown) indicating a parameter or property of the blood sample (not shown) that relates to the clotting capacity or state of the blood sample (not shown) in the well 12.

Figure 3:
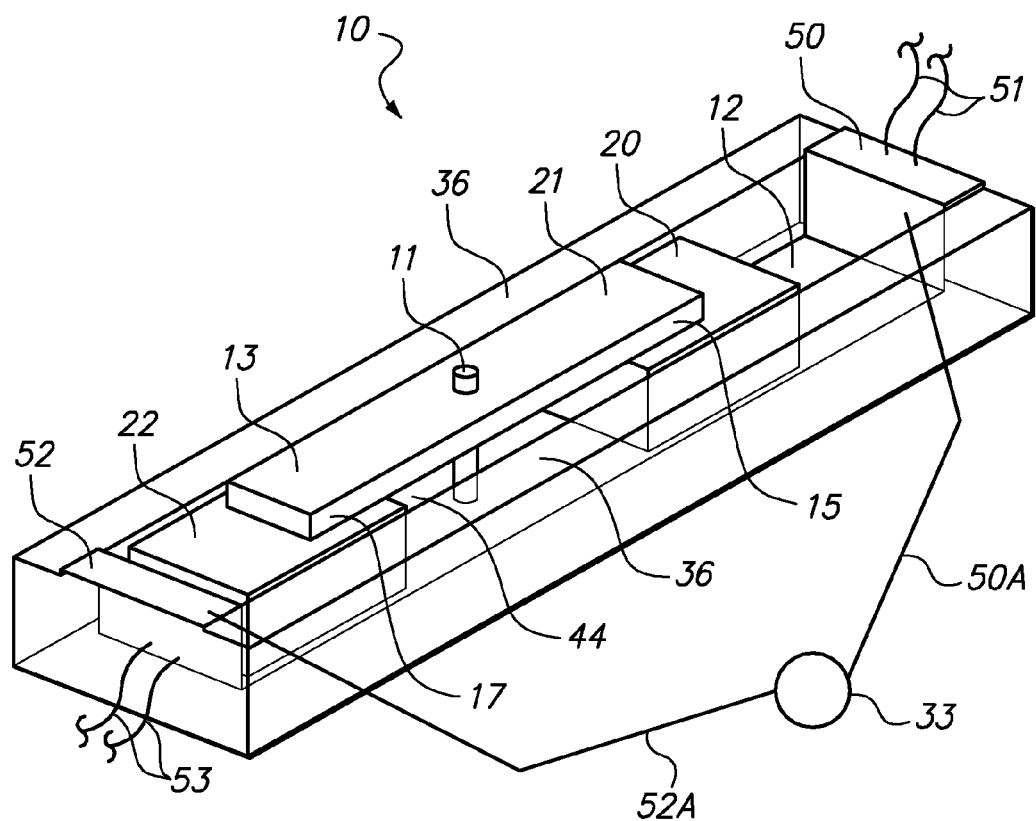
FIG. 3 is a perspective view of an embodiment of a blood coagulometer having electromagnets to reciprocate a carriage having a wetted member disposed within a well for receiving a blood sample.

FIG. 3 is a perspective view of an alternate embodiment of a blood coagulometer 10 of the present invention having two electromagnets 50 and 52 that cooperate to magnetically position and/or to reciprocate a carriage 21 having a wetted member 11 disposed within a well 12 defined between walls 36 for receiving a blood sample (not shown). The wetted member 11 is connected to a retainer 13 and extends from the retainer 13 downwardly into the well 12. The retainer 13 is supported at a first end 15 on a first low friction support 20 and at a second end 17 on a second low friction support 22. The first low friction support 20 and the second low friction support 22 are, for example, polished and lightweight members that slide on a polished floor 44. In one embodiment of the apparatus 10 of the present invention, the carriage 21, for example, the first low friction support 20 and/or the second low friction support 22, comprises one or more magnetic materials that respond to electrically-generated magnetic fields produced by electrically exciting the first electromagnet 50 and the second electromagnet 52 to together produce a magnetic field(s) that act upon the magnetic materials of the first low friction support 20 and/or the second low friction support 22 to thereby move the carriage 21 and to thereby move the wetted member 11 within the blood sample (not shown) therebelow. The retainer 13 and the first and second low friction supports 20 and 22 together provide a carriage 21, and the first electromagnet 50 and the second electromagnet 52, together with the first and second low friction supports 20 and 22, enable the controller 33 to controllably move the carriage 21 and to thereby move the wetted member 11 within the blood sample (not shown) received in well 12. It will be understood that the controller 33 may generate a first signal 50A to the first electromagnet 50 and a second signal 52A to the second electromagnet 52 and thereby control the electrical current to the first electromagnet 50 provided by wires 51 and to control the electrical current to the second electromagnet 52 provided by wires 53.

FIG. 3 illustrates the carriage 21 after the controller 33, the first electromagnet 50, the second electromagnet 52, the first low friction member 20 and the second low friction member 22 are together used to generate a magnetic force on the magnetic material of one or both of the first low friction member 20 and the second low friction member 22 to displace the carriage 21 to a position distal to the first electromagnet 50 and proximal to the second electromagnet 52. It will be understood that by, for example, using the controller 33 to reverse the polarity of the electrical currents provided via wires 51 to the first electromagnet 50 and via wires 53 to the second electromagnet 52, the carriage 21 can be magnetically re-positioned to a position proximal to the first electromagnet 50 and distal to the second electromagnet 52. This cycle can be repeated at a rate controllable by the controller 33 and the signals 50A and 52A generated thereby.

In normal operation, the carriage 21 of the embodiment of the blood coagulometer 10 of FIG. 3 is reciprocated between a first position illustrated in FIG. 3, with the carriage 21 proximal to the second electromagnet 52, to a second position, with the carriage 21 proximal to the first electromagnet 50, by providing a first electrical current through wires 51 creating a magnetic field around electromagnet 50 that repels the magnetic material of the first low friction support 20 and/or by providing a second current through wires 53 creating a magnetic field around electromagnet 52 that attracts the magnetic material of second low friction support 22, and by then providing a reversed current through wires 51 creating a reversed magnetic field around electromagnet 50 that attracts the magnetic material of the first low friction support 20 and/or by providing a second reversed current through wires 53 creating a magnetic field around electromagnet 52 that repels the magnetic material of second low friction support 22. This process can be repeated to reciprocate the wetted member 11 within a blood sample received within the well 12. The force applied by operation of the electromagnets 50 and 52 can be determined using physical and electrical properties of the electromagnets 50 and 52, the currents provided via wires 51 and 53, the mass of the carriage 21 and the frictional resistance to movement of the first low friction support 20 and the second low friction support 22.

Figure 4:
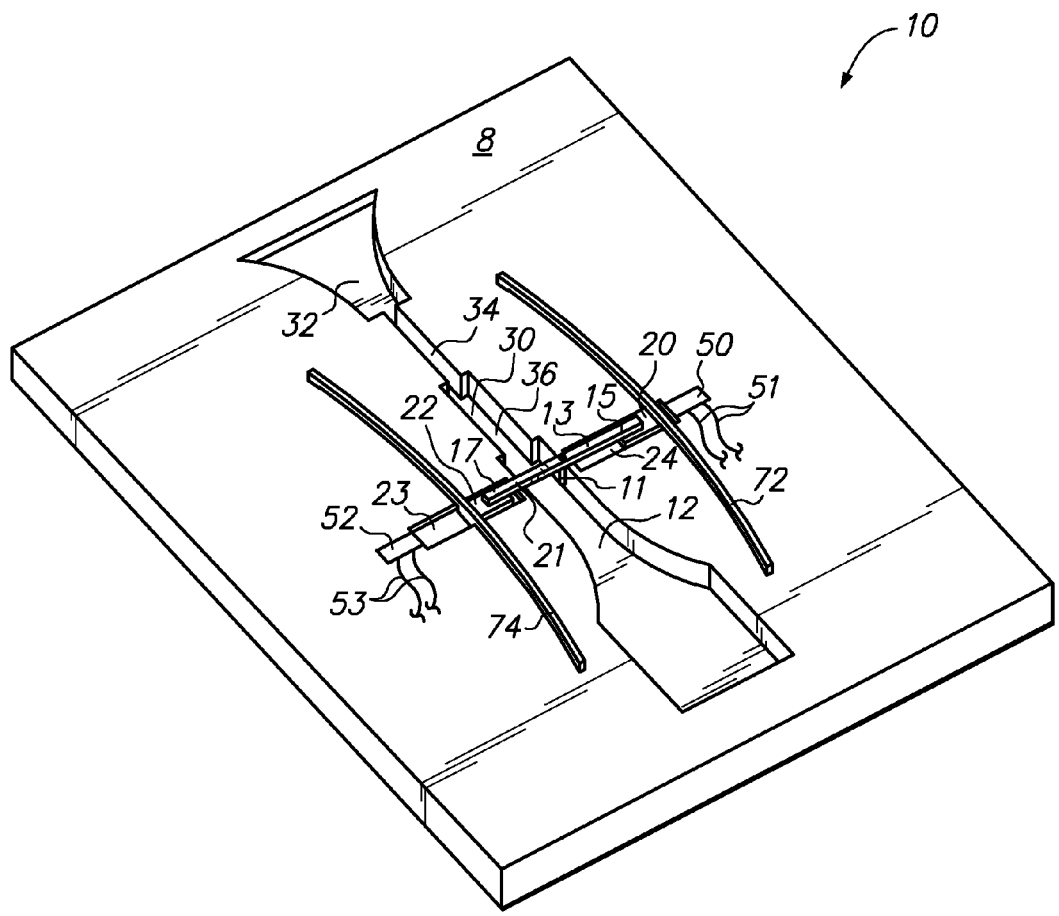
FIG. 4 is a perspective view of an embodiment of a blood coagulometer of the present invention having electromagnets to move a carriage having a wetted member disposed within a well for receiving a blood sample and leafs to support the carriage to reduce friction and to increase carriage response to electromagnetic forces.

FIG. 4 is a perspective view of an embodiment of a blood coagulometer 10 of the present invention having a first electromagnet 50 and a second electromagnet 52 to move a carriage 21 having a wetted member 11 disposed within a well 12 for receiving a blood sample (not shown) and flexible leafs 72 and 74 to provide support the carriage 21 to reduce friction upon movement of the carriage 21 and to thereby increase the responsive movement of carriage 21 in response to electromagnetic forces generated by the activation of the first electromagnet 50 and the second electromagnet 52. The retainer 13 is supported at a first end 15 by a first low friction support 20 and at a second end 17 by a second low friction support 22. The wetted member 11 extends downwardly from the retainer 13 into the well 12 that receives the blood sample (not shown). The blood coagulometer 10 of FIG. 4 also includes a first electromagnet 50 with wires 51 to provide an activating current to the first electromagnet 50 and a second electromagnet 52 with wires 53 to provide an activating current to the second electromagnet 52. The embodiment of the blood coagulometer 10 of FIG. 4 comprises a first channel 24 in which the first low friction support 20 reciprocates and a second channel 23 in which the second low friction support 22 reciprocates. The movement of the carriage 21 in the embodiment of the blood coagulometer 10 of FIG. 4 is effected by supplying a current through wires 51 to the first electromagnet 50 and by supplying a second current through wires 52 to the second electromagnet 52. It will be understood that the current(s) provided through wires 51 and wires 52 may be variable and/or reversible to position the carriage 21. The first low friction support 20 and/or the second low friction support 22 comprise a magnetic material to provide responsiveness to magnetic fields generated by electrical activation of the first electromagnet 50 and the second electromagnet 52. Leafs 72 and 74 may, in one embodiment, elongate members with a rectangular cross-section that are very flexible and easily bent in the direction of movement of the carriage 21 but resistant to bending in the direction perpendicular to the direction of movement of the carriage 21. The leafs 72 and 74 provide support to the first low friction member 20 and the second low friction member 22 to enhance responsiveness of the carriage 21 to magnetic fields generated by the first electromagnet 50 and the second electromagnet 52. In one embodiment, leafs 72 and 74 may, in addition, comprise springs that receive and store energy as the carriage 21 is displaced by magnetic force applied by one or both of the first electromagnet 50 and the second electromagnet 52 from the position illustrated in FIG. 4, with the first low friction support 20 disposed proximal to the first electromagnet 50 and the second low friction support 22 separated from the second electromagnet 52, to a second position with the second low friction support 22 proximal to the second electromagnet 52 and the first low friction support 20 separated from the first electromagnet 50. Energizing one or both of the first electromagnet 50 and the second electromagnet 52 by providing a current(s) via wires 51 and 53, respectively, generates a magnetic field that displaces the carriage 21 from the position illustrated in FIG. 4 towards the second electromagnet 52. Reversing the current(s) provided to the first electromagnet 50 though wires 51 and/or to the second electromagnet 52 through wires 53 restores the carriage 21 to or towards the original position shown in FIG. 4.

Figure 5:
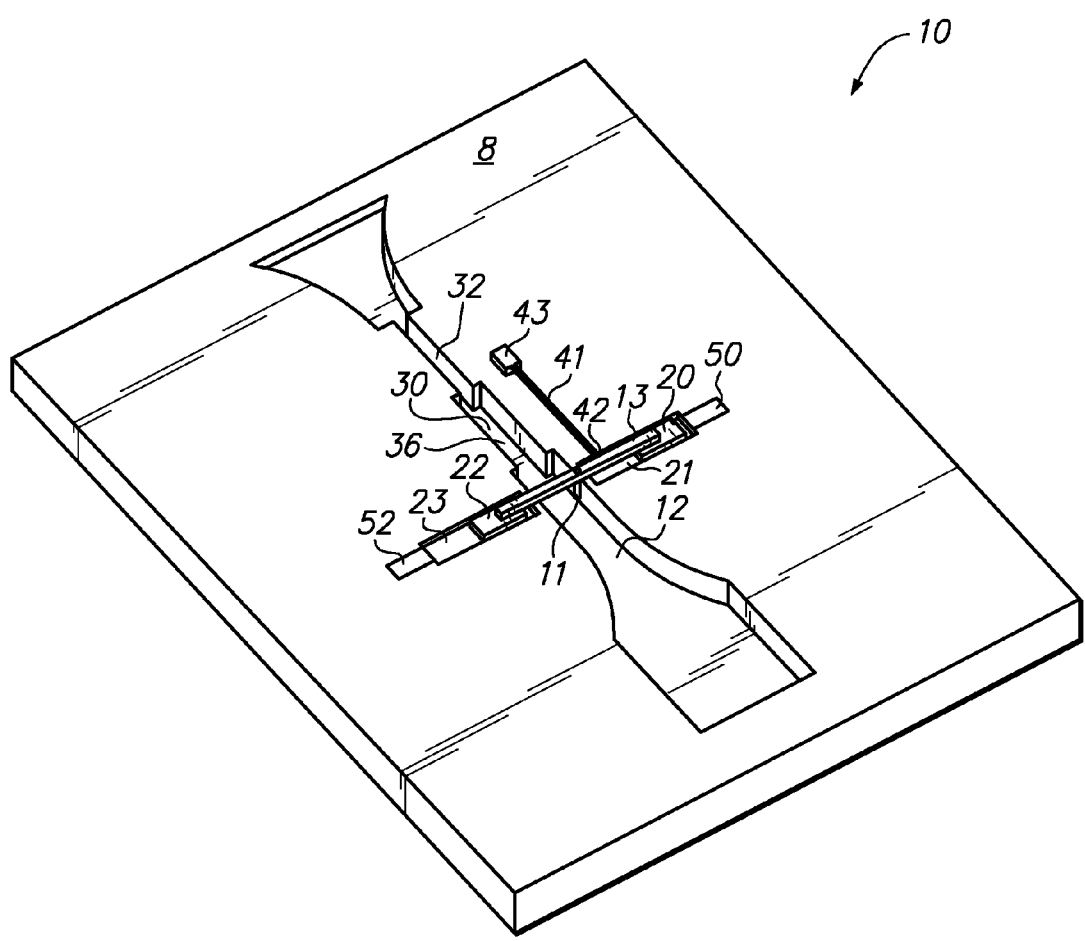
FIG. 5 is a perspective view of an embodiment of a blood coagulometer of the present invention constructed similarly to the embodiment of FIG. 4 but having a pivoting carriage support instead of the leaf supports.

FIG. 5 is a perspective view of an embodiment of a blood coagulometer 10 of the present invention constructed similarly to the embodiment of FIG. 4 but having a pivoting carriage support 41 instead of the leafs 72 and 74 illustrated in FIG. 4. The embodiment of the blood coagulometer 10 of FIG. 5 includes a pivoting support base 43 secured to the tray 8 and pivotally connected to the carriage 21 of the blood coagulometer 10 through the pivoting carriage support 41. The pivoting support base 43 and the pivoting carriage support 41 operate to support the carriage 21 and to reduce friction upon movement of the carriage 21, thereby increasing the responsiveness of the carriage 21 to forces generated by the first electromagnet 50 and/or the second electromagnet 52.

Figure 6:
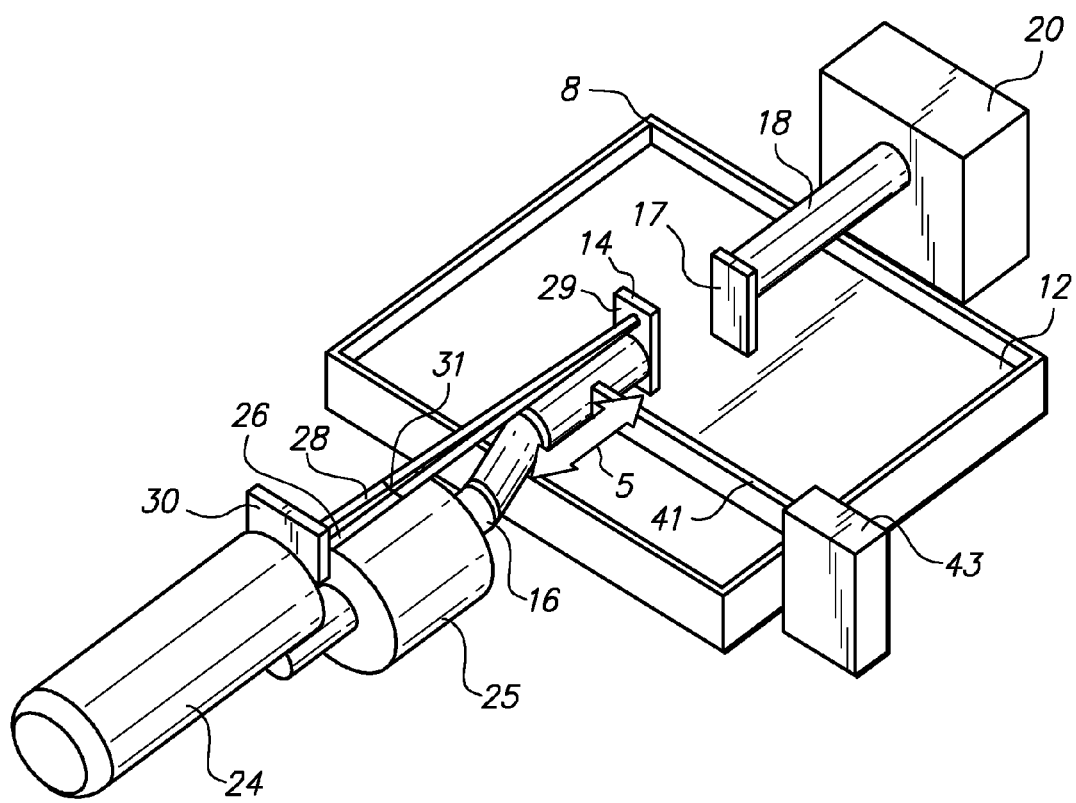
FIG. 6 is a perspective view of an embodiment of a blood coagulometer similar to the embodiment of FIG. 1.

FIG. 6 is a perspective view of an embodiment of a blood coagulometer 10 similar to the embodiment of FIG. 1. The blood coagulometer 10 of FIG. 6 comprises a tray 8, a reflective member 29 on the primary wetted member 14 supported by a primary support beam 16 that is turned 90 degrees to the similar reflective member 29 illustrated in FIG. 1 as being on the primary support beam 16. The laser element 24 of FIG. 6 is positioned such that the incident beam 26 produced by the laser element 24 is generally aligned with the primary support beam 16 that supports the primary wetted member 14. The reciprocation of the primary wetted member 14 is generally along the path of arrow 15. The secondary wetted member 17 is not necessary for the primary function of the apparatus 10, but may be added to allow clot adhesion of the sample of blood (not shown) received in the well 12 to be measured, as discussed above.

Figure 7:
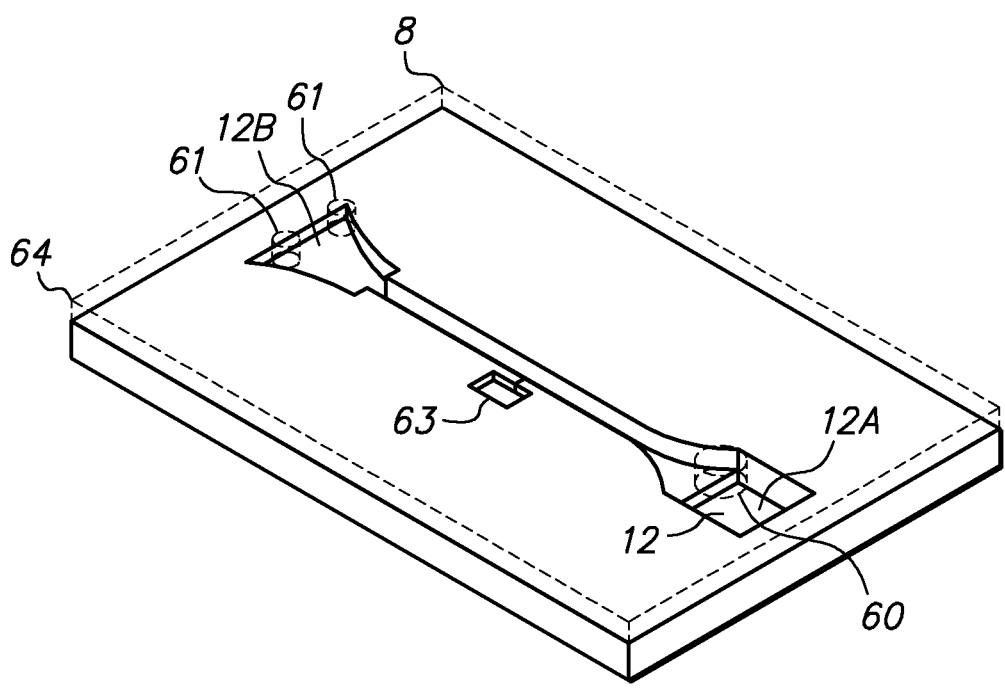
FIG. 7 is a perspective view of the tray of FIGS. 4 and 5 showing the desired location of a fill hole and a pair of vent holes that may be included in a tray cover, for example, a transparent tray cover, for use in connection with the apparatus of the present invention.

FIG. 7 is a perspective view of the tray 8 of FIGS. 4 and 5 showing the desired location of a blood fill hole 60 and a pair of air vent holes 61 that may be included in a tray cover 64, for example, a transparent tray cover, for use in connection with the apparatus 10 of the present invention. The blood fill hole 60 in the tray cover 64 is aligned with the receiving end 12A of the well 12 and the air vent holes 61 are aligned with the waste end 12B of the well 12. The tray 8 further includes a component recess 63 to receive a prefabricated component of the apparatus 10 such as, for example, the actuator 25 (see FIGS. 1, 2 and 6), a deflection sensor 27 (see FIG. 2) or a stationary member 20 (see FIG. 1). It will be understood that a plurality of prefabricated component recesses 63 can be manufactured into the tray 8 for advantageous assembly of the apparatus 10.

Figure 8:
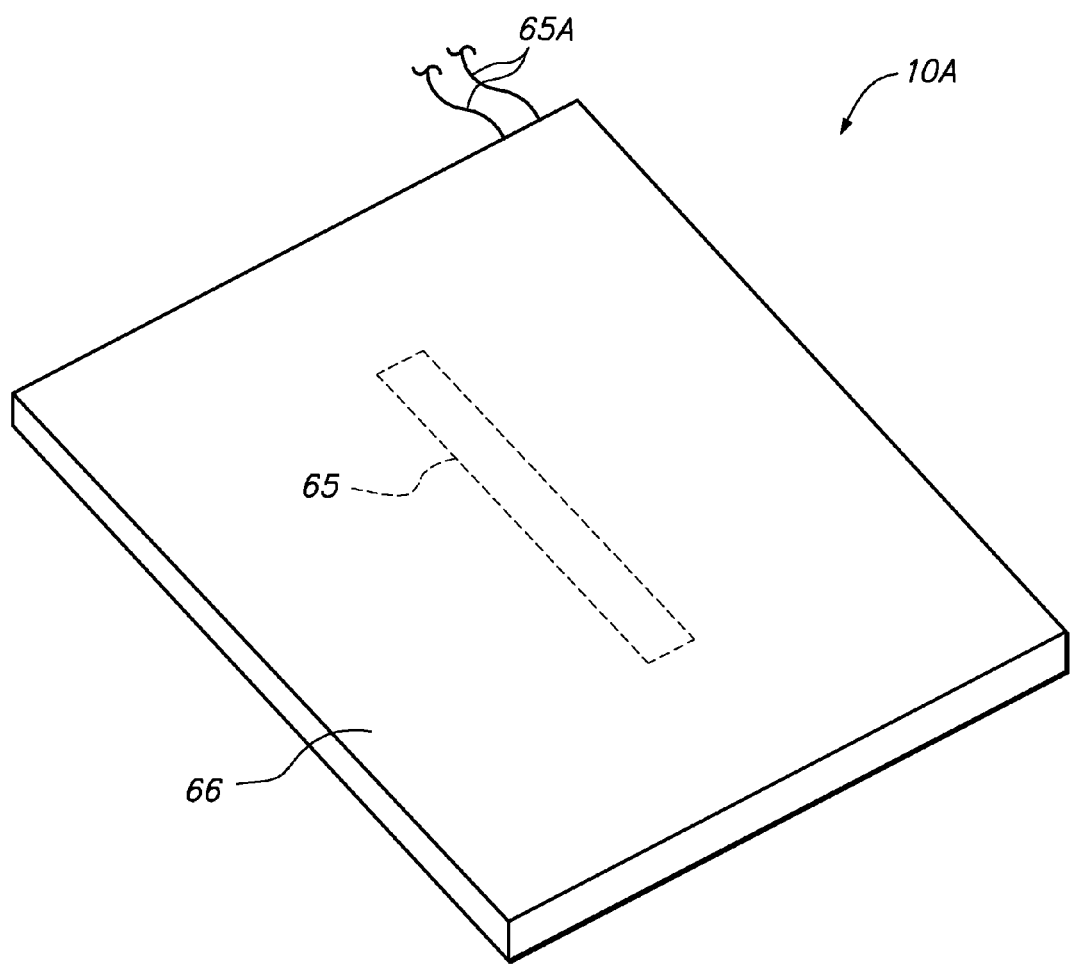
FIG. 8 is a perspective view of an interior surface of a tray cover of the present invention for use in connection with the apparatus of FIGS. 3, 4 and 5 and including an image sensor such as, for example, a charge-coupled device (CCD) image sensor or a complementary metal-oxide-semi-conductor active pixel (CMOS) image sensor.

FIG. 8 is a perspective view of an interior surface 66 of a tray cover 10A of the present invention for use in connection with the apparatus of FIGS. 4 and 5 and including a sensor 65 such as, for example, a charge-coupled device (CCD) image sensor or a complementary metal-oxide-semiconductor active pixel (CMOS) image sensor. The tray cover 10A of FIG. 8, when the tray cover 10A is received onto the apparatus 10 of FIGS. 4 and 5, would position the sensor 65 on the interior surface 66 of the tray cover 10A directly over the range of movement of the wetted member 11 (see FIGS. 4 and 5). The sensor 65 is coupled to the sensor wires 65A that are connectable to a processor (not shown) and the sensor 65 generates a signal to a processor (not shown) indicating the position of the wetted member 11. This arrangement enables the processor (not shown) to compare the actual position of the wetted member 11 supported on the carriage 21 of FIGS. 4 and 5 with the theoretical position of the wetted member 11 but for the resistance to movement imparted to the wetted member 11 by the clotting blood (not shown in FIGS. 4 and 5) received in the well 12. It will be understood that the difference between the actual position of the wetted member 11 and the theoretical position of the wetted member 11 is attributable to the resistance to movement of the wetted member 11 through the clotting blood sample.

An alternative sensor 65 may be a magnet sensor that detects the position of a magnetic wetted member 11, an optical sensor that detects an optically detectable color on the wetted member 11, or some other sensor that can be used to detect the actual position of the wetted member 11 within the range defined by the length of the sensor 65 on the interior 66 of the tray cover 10A. The sensor 65 may include multiple or redundant means of detecting the position of the wetted member 11 or of another feature on the carriage 21 of the apparatus 10 of FIGS. 4 and 5.

It will be understood that the embodiments of the blood coagulometer 10 of FIGS. 3 through 5 operate by magnetically imparting a determinable displacing force on the carriage 21 by energizing one or both of the electromagnets 50 and 52. The current supplied to the electromagnets 50 and 52 is easily determined, and the magnetic field(s) generated by energizing the electromagnets 50 and 52 is therefore also determinable with great accuracy. The magnetic and physical properties of the magnetic materials can also be determined with accuracy, and the net force imparted to the carriage 21, along with the mass of the carriage 21, enables the determination of the theoretical unimpeded displacement of the carriage 21 that would occur in response to the determinable magnetic fields were it not for the resistance to displacement caused by the wetted member 11 moving through the blood sample (not shown) within the well 12 (in FIGS. 4 and 5). The sensor 65 illustrated in FIG. 8 can be used to detect the actual position of the carriage 21 at any given instant. The actual position can be compared to the theoretically determined position that would occur but for the resistance to movement of the wetted member 11 extending from the carriage 21, and a resistance to movement of the wetted member 11 through the blood sample (not shown) can be determined. In this manner, the resistance can be correlated to the dotting capacity of the blood sample (not shown), which may vary (most likely, increase) with subsequent determinations.

One novel feature of one of the above-disclosed apparatuses of the present invention, from which multiple functional improvements accrue, is the usage of a support beam versus a torsion wire, as used in conventional TEG devices, to transmit mechanical force from an actuator to the blood sample. The support beam allows the measurement of the movement of the wetted member 11 (in the embodiments illustrated in FIGS. 3, 4 and 5) and primary wetted member 14 (in the embodiments illustrated in FIGS. 1, 2 and 6) as it is driven easily at physiologic rates (e.g., 120 cycles per minute or 2 Hz). It will be understood that the frequency of 120 cycles per minute may correlate to the rate of beating of human heart of a patient in hemorrhagic shock. Unlike torsion wires, which are optimally driven in a narrow frequency range, the actuator 25 driven primary support beam 16 (in the embodiments illustrated in FIGS. 3, 4 and 5) and the electromagnetically positioned carriage 21 (in the embodiments illustrated in FIGS. 1, 2 and 6) allow a wide range of drive frequencies which allow determination of differential coagulation data under varying shear rates. Shear rate is known to influence blood coagulation, but conventional blood coagulometers do not allow investigation of this rheological blood property.

Alternatively, the wetted members 11 and 14 and support beam 16 may be driven directly along the axis of the actuator 25, as indicated by the arrow 15 in FIG. 6. In this configuration, the support beam 16 serves as a support strut that can also operate as a return spring. This configuration simplifies the mechanical action of the wetted member 14 (linear rather than arcuate). A conventional torsion-wire blood coagulometer is limited by its rotational design to a sinusoidal drive pattern. The rigid structure of the actuator 25 and support beam 16 or even highly turbulent manner. The support beam 16, as disclosed herein, allows the wetted member 14 to be driven in a non-sinusoidal or even a highly turbulent manner. A reciprocating movement of the wetted member 14 is easily achieved by the linear actuator 25 of embodiments of the present invention. If a rotary actuator is used, the wetted member may move in an arc fashion within a toroidal channel. Although blood flow within vessels is generally accepted to be laminar in nature and, hence, appropriately simulated by a sinusoidal pattern that mimics the actual pulse, the flow at the site of a hemorrhage is certainly turbulent; thus, a sinusoidal drive pattern may not be appropriate for eliciting coagulation parameters that are relevant in hemorrhage.

The rigid electromagnetic actuator/support beam combination allows an arbitrary waveform to be used to drive the measurement wetted member, in order to determine clotting parameters that may differentially influence clot formation under conditions of turbulent flow as expected at the site of hemorrhage. Unlike the disclosed techniques, conventional TEG devices are highly sensitive to physical disturbance and require re-calibration prior to each measurement. A support beam-type embodiment of the present invention illustrated in FIG. 6 potentially allows the measuring wetted member to be driven at much higher rates. This measurement regime is used to investigate mechanical resonance of clot structure during formation of dot (resonant frequency is known to change during polymerization processes). This type of test is not achievable by a standard torsion-wire coagulometer because of limitations of drive frequency. An additional advantage is that the support beam can be overdriven to determine clot rupture strength. In one embodiment, the support beam, or a portion of the beam, can be replaced with a strain gauge to measure deflection. The support beam structure allows, in an alternative embodiment, support beam deflection to be determined by bonding a strain gage or similar apparatus to the support beam. This simplifies the measurement apparatus versus using, for instance, reflected light to measure deflection. A further benefit of the presently disclosed designs versus that of conventional TEG devices is that it can be constructed using photolithographic and other micro-scale manufacturing processes.

Micro-electromechanical may be fabricated from a variety of materials and substrates, silicon (Si), silicon nitride ($Si_3N_4$), silicon-on-insulator, glass or polymers and may be fabricated using photolithography, deep reactive ion etching, and similar processes. Microelectromechanical electromagnets and support beams may be constructed from a variety of materials and substrates, and may be fabricated using photolithography, deep reactive ion etching, anisotropic wet or dry etching techniques to undercut the support beam structure and similar processes.

The utilization of these fabrication methods results in two major benefits relative to the problem of measuring blood coagulation parameters. First, and most obviously, the size of the measuring apparatus can be reduced dramatically, allowing a smaller device (with better portability) and a smaller blood sample volume. The reduction in blood sample volume actually devolves from two aspects of the device design including the suitability for production using micro-scale manufacturing processes and the ability to have an arbitrary shape for the sample well.

The sample well holds the blood sample in position for interaction with the wetted member. The dimensions of the sample well are preferred to be no larger than ten times that of the measurement vane for sensitivity of compression measurement. Surface energy may be altered to help blood sample wet the sample well, but this is not a crucial functional characteristic The reduction of blood sample volume extends the utility of viscosity-based blood coagulation measurement in the neonatal critical care realm and extends the range of applicability to allow use of TEG in small animal models, something which is not possible with conventional TEG devices. The neonatal and research use of TEG is limited by the requirement for a 1-3 ml sample of blood because that volume is physiologically deleterious for the patient or research animal.

A second benefit of the use of micro-scale manufacturing methods is reproducibility. The torsion constant of the wire in conventional TEG devices is carefully chosen in order to allow sensitive measurement in a very specific regime of simulated blood flow. However, the process of producing and mounting the torsion wire results in a range of actual torsion constants in production, such that conventional torsion wire TEG devices require quality assurance calibration for each individual measurement wire. In practice, these TEG wires are disposable, and the machine must be re-calibrated for each sample run. The resulting increase in test time, personnel costs and uncertainty in interpretation have limited the acceptance of conventional TEG devices despite the fact that most, if not all, comparative studies show that conventional TEG devices are superior to conventional coagulation studies (PT, PTT, INR) for management of bleeding. In contrast to a torsion wire, a die-based support beam constructed using modern fabrication methods is highly repeatable in its relevant spring and other mechanical characteristics, which can be simple, complex or nonlinear. Since no inter-sample calibration is necessary by the end user, this method will reduce the overall cost for mechanical testing of coagulation.

A preferred embodiment of the apparatus of the present invention is fabricated using micro-scale manufacturing processes. The actuator most appropriate for this embodiment is a micro-electromechanical electromagnetic actuator. The combination of micro-electromechanical actuator, support beam/wetted member, and deflection sensor and/or strain gauge and/or position sensor, all fabricated onto a single tray (and in some embodiments the active portions of the device are sealed), to allow the apparatus to be scaled into a rugged, point-of-care diagnostic device. This overall scheme is superior for measurement accuracy because the actuator is directly coupled to the measurement substrate (the clot), and does not depend on the large torsional compliance of the wire to overcome micro-movement limitations of the rotational actuator used for conventional TEG devices. The wetted member can potentially be driven with a slowly increasing current in a constant displacement mode. The plot of the drive current over time is another method of delineating the coagulation curve. Secondary wetted members can be added to measure other parameters, such as clot adhesion.

The wetted member surfaces can be bound with, for instance, bioactive proteins such as, but not limited to, antibodies to deter or enhance platelet adhesion or fibrin adhesion, should this be desirable. This allows selected modifications to the device which facilitates the determination of specific sub-parameters of clot formation (fibrin formation versus platelet function).

Deflection of the wetted member can be simultaneously measured by several techniques. The deflection of the driven wetted member reflects the strength of clot encountered by the wetted member, while deflection of the secondary wetted member will be a measure of clot adhesion. One or more secondary measurement wetted members may be added to measure other parameters of coagulation, such as clot adhesion, that are not available with conventional TEG devices.

Extreme reduction in wetted member and blood sample size could potentially allow the probing of small-scale interactions that result in larger clot formation. Since the drive mechanism of embodiments of the apparatus of the present invention is electromechanical (as opposed to purely mechanical via the torsion wire), any necessary calibration can occur in software, rather than having to re-calibrate the scale prior to each use, as is required for conventional torsion wire TEG devices. The system may also run in constant displacement mode and the actuator current may be plotted to reflect clot strengthening. Since no external personnel for quality assurance are necessary, this method will supplant existing methods for mechanical blood coagulation analysis in real-world laboratories; that is, this method will dramatically reduce the real-world cost for mechanical testing of blood coagulation.

The measurement of blood coagulation parameters may be made with the apparatus and method of the present invention and a sample of blood. A set of refinements of this general method includes separate measurement of clot strength and adhesion, a reduction of measurement apparatus into Si-based mass-produced and disposable for hand-held measurement devices, and an improved mathematical description of the measured quantities.

For example, the embodiment of FIG. 3 shows a schematic drawing of the disposable unit, which may be mass produced at low cost via thin-film/photolithography and related micro-scale techniques. A silicon die may be constructed with a central well and two support beamed (or hinged) beams that hold wetted members within the well. The central well may be prefilled with clot activator and then with a sample of blood prior to use. An electromagnetic MEMS actuator may be used to drive one of the wetted members through a shallow angle, analogous to the movement of the central stylus in the original description of the TEG.

The curve defined by the amount of wetted member deflection, x, over time will reflect the development of clot and its subsequent lysis. Traditional TEG devices use geometric methods to determine a group of angles and amplitudes that reflect measures of clotting. However, the measurement apparatus actually determines the rate of the underlying mixed-order chemical reaction whose is end product is clot. As such, it is more properly described by the calculus of chemical reaction kinetics. Under this framework, the dynamic equilibrium of coagulation and lysis may be described mathematically. The reaction rate is defined as $dx/dt$, with positive values signifying the generation of new clot and negative values signifying lysis of clot. The second derivative will then give information about the rate at which the system tips towards lysis or coagulation, with $d2x/dt2>0$ indicative of shift towards increasing coagulation and $d2x/de<0$ implying the system is trending towards increased lysis. The local maximum and local minimum values of $d2xt/dt2$ reflect the states of maximum coagulation and maximum lysis, respectively, achievable by the patient's blood chemistry at the time the sample was drawn.

The device and methods described herein allow the wetted member to be driven with a range of known forces. This aspect of the design allows, in addition to the well-described parameters of the conventional TEG tracing, determination of the well understood physical parameters, viscosity and elastic modulus. Viscosity is not directly measured in conventional TEG devices, but it clearly increases during the early stages of clot formation (polymerization). As fibrin is cross-linked, the solidifying dot begins to display increases in elastic modulus. A known force, combined with measured displacement and velocity of the vane, allows determination of viscosity and elastic modulus, potentially allowing greater insight into the physical process of clot formation.

Although specific embodiments of the invention have been described herein in some detail, this has been done solely for the purposes of explaining the various aspects of the invention, and is not intended to limit the scope of the present invention, which is limited only by the claims which follow. Those skilled in the art will understand that the embodiment shown and described is exemplary, and various other substitutions, alterations and modifications, including but not limited to those design alternatives specifically discussed herein, may be made in the practice of the invention without departing from its scope.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, components and/or groups, but do not preclude the presence or addition of one or more other features, integers, steps, operations, elements, components, and/or groups thereof. The terms "preferably," "preferred," "prefer," "optionally," "may," and similar terms are used to indicate that an item, condition or step being referred to is an optional (not required) feature of the invention.

The corresponding structures, materials, acts, and equivalents of all means or steps plus function elements in the claims below are intended to include any structure, material, or act for performing the function in combination with other claimed elements as specifically claimed. The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. An apparatus to measure clotting in a blood sample, comprising:
   a tray;
   a well in the tray to receive a sample of the blood;
   a support beam connected at a first end to the tray and connected at a second end to a wetted member to support the wetted member at least partially within the well;
   a linear motor connected between the tray and the support beam and activatable by application of an electrical current to impart a force, corresponding in magnitude to the applied current, on the support beam to move the support beam relative to the tray and to thereby move the wetted member within the well; and
   a deflection sensor coupled to the tray to measure the deflection of the support beam resulting from resistance to movement of the wetted member imparted by the sample of blood received in the well;
   wherein the measured deflection of the support beam resulting from the resistance to movement of the wetted member within the sample of blood in the well is correlated to a capacity of the blood to clot.

2. The apparatus of claim 1, wherein the linear motor comprises:
   an electrically-powered linear motor having at least one conductive coil through which the electrical current flows; and
   at least one magnet disposed on a connecting rod movable within the at least one conductive coil;
   wherein the application of a current having a first polarity to the linear motor causes the connecting rod to be moved in a first direction against the support beam; and
   wherein the application of a current having a second polarity, opposite to the first current, causes the connecting rod to be moved in a direction opposite to the first direction.

3. The apparatus of claim 1, wherein the support beam is an elastically flexible elongate shaft.

4. The apparatus of claim 1, wherein the electrically-powered linear motor is connectable to a battery.

5. The apparatus of claim 4, wherein the tray comprises a battery portion to receive and secure a battery to the tray.

6. The apparatus of claim 1, wherein the deflection sensor comprises:
   a laser element coupled to the tray to generate an incident beam;
   a reflective member on the support beam; and
   a photo-detector array coupled to the tray and connectable to a controller;
   wherein the photo-detector array generates a signal to the controller indicating the location of impingement on the photo-detector array of a reflected beam, and the signal enables the determination of the angle between the incident beam and the reflected beam;
   wherein the angle between the incident beam and the reflected beam indicates the deflection of the support beam resulting from the resistance to movement of the wetted member within the well as force is imparted by the linear motor to the support beam; and
   wherein the angle between the incident beam and the reflected beam can be correlated to the clotting capacity of the blood.

7. The apparatus of claim 1, wherein the deflection sensor comprises:
   a strain gauge coupled to the support beam to generate a signal to a processor corresponding to the stress imparted to the support beam as a result of the resistance to movement of the wetted member within the well as force is imparted by the linear motor to the support beam;
   wherein the signal generated by the strain gauge can be correlated to the clotting capacity of the blood.

8. The apparatus of claim 1, further comprising:
   a controller to receive a signal corresponding to the measured deflection and generated by the deflection sensor and to generate a display signal; and
   a display device coupled to the tray and connected to receive the display signal from the controller.

9. The apparatus of claim 8, wherein the display device is one of a light emitting diode display device, a liquid crystal display device or a gauge.

10. An apparatus to measure clotting in a blood sample, comprising:
    a tray;
    a well in the tray to receive a sample of the blood;
    a carriage, having a first end, a second end, a magnetic material and a wetted member movably supported on the tray to support at least a portion of the wetted member within the well;
    an electrically-powered motor comprising:
       at least a first electromagnet connectable to an electrical current source;
       wherein energizing the first electromagnet creates a magnetic field that imparts a corresponding force on the magnetic material of the carriage to move the carriage and to thereby move the wetted member within the well, and a deflection sensor coupled to the tray to measure the deflection of the carriage resulting from resistance to movement of the wetted member imparted by the sample of blood received in the well;

wherein the measured deflection of the carriage resulting from the resistance to movement of the wetted member within the sample of blood in the well is correlated to a capacity of the blood to clot.

11. The apparatus of claim 10, wherein the motor further comprises:

a second electromagnet connectable to an electrical current source;

wherein energizing the first and second electromagnets creates a magnetic field that imparts a corresponding force on the magnetic material of the carriage to move the carriage and to move the wetted member within the well.

12. The apparatus of claim 10, wherein the deflection sensor comprises:

a laser emitting element coupled to the tray to generate an incident beam;

a photo-detector array connected to a controller; and a reflecting member coupled to the carriage to reflect the incident beam to provide a reflected beam of laser light onto the photo-detector array;

wherein the controller senses the location of impingement of the reflected beam on the photo-detector array, determines an angle between the incident beam and the reflected beam, and calculates the position of the carriage resulting from the force applied to the magnetic material of the carriage; and wherein the controller compares the calculated position of the carriage to a theoretical position of the carriage determined based on the carriage mass and the known force applied to the magnetic material by the first electromagnet.

13. The apparatus of claim 12, wherein the theoretical position of the carriage and the detected position of the carriage are compared to indicate the clotting capacity of the sample of blood received in the well.

14. The apparatus of claim 12, wherein the controller receives a signal corresponding to the measured deflection and generated by the deflection sensor and generates a display signal; and further comprising a display device connected to receive the display signal from the controller.

15. The apparatus of claim 14, wherein the display device is one of a light emitting diode display device, a liquid crystal display device or a gauge.

16. A method of testing a sample of blood to determine the clotting capacity of the blood, comprising:

providing a tray having a well;

receiving, into the well, a sample of the blood to be analyzed;

connecting, a wetted member to a first portion of a support member;

movably supporting the support member on the tray and above an interface between the sample of blood and air to dispose at least a portion of the wetted member within the sample of blood and below the interface;

imparting a known force to the support member to substantially linearly displace the portion of the support member, and the wetted member connected thereto, relative to the well to move the wetted member within the sample of blood;

determining a theoretical displacement of the wetted member corresponding to the known force imparted to the support member;

measuring the displacement of the wetted member as a result of the known force imparted to the support member;

comparing the measured displacement of the wetted member within the sample of blood to the theoretical displacement to determine a resistance to displacement of the wetted member attributable to the sample of blood; and correlating the resistance to displacement of the wetted member to a clotting capacity of the sample of blood.

17. The method of claim 16, further comprising:

imparting a second known force to the support member;

determining a theoretical displacement of the wetted member corresponding to the second known force imparted to the support member;

measuring the displacement of the wetted member as a result of the second known force imparted to the support member;

comparing the measured displacement of the wetted member within the sample of blood to the theoretical displacement to determine a resistance to displacement of the wetted member attributable to the sample of blood; and correlating the resistance to displacement of the wetted member to a clotting capacity of the sample of blood.

18. The method of claim 17, wherein the second known force equal to the previously imparted known force.

19. The method of claim 16, wherein imparting a known force to the support member to displace the portion of the support member, and the wetted member connected thereto, relative to the well to move the wetted member within the sample of blood comprises:

providing on the tray at least one electromagnet activatable to produce a magnetic field upon activation;

providing at least one magnetic material on at least one of the support member and the wetted member; and activating the electromagnet using a known current to impart a known force on the magnetic material.

20. The method of claim 16, wherein measuring the displacement of the wetted member as a result of the known force imparted to the support member comprises:

providing a laser element on the tray;

providing a reflective member on one of the support member and the wetted member;

providing a photo-detector array on the tray;

emitting laser light from the laser element to direct an incident beam onto the reflective member as the known force is imparted to the support member;

using the photo-detector array to generate a signal corresponding to a location on the photo-detector array of impingement of a reflected beam from the reflective member;

using a controller to receive the signal and to determine an angle between the incident beam and the reflected beam; and correlating the determined angle between the incident beam and the reflected beam with a resistance to movement of the wetted member imparted by the blood and to the clotting capacity of the blood.

21. The method of claim 16, wherein measuring the displacement of the wetted member as a result of the known force imparted to the support member comprises:
- providing a tray cover having an interior side with an image sensor;
- disposing the tray cover onto the tray to position the image sensor above a range of movement of the support member;
- using the image sensor to determine the position of the support member as the known force is imparted to the support member;
- using the image sensor to generate a signal corresponding to a location of the support member;
- using a controller to receive the signal and to determine the position of the support member;
- comparing the position of the support member to a theoretical position of the support member; and
- correlating the difference between the position of the support member and the theoretical position of the support member with a resistance to movement of the wetted member imparted by the blood and to the clotting capacity of the blood.

* * * * *